(12) United States Patent
Visser et al.

(10) Patent No.: US 9,615,928 B2
(45) Date of Patent: Apr. 11, 2017

(54) MEDICAL DEVICE FOR RECONSTRUCTION OF A HUMERUS FOR THE OPERATIVE TREATMENT OF A PROXIMAL HUMERUS FRACTURE

(71) Applicant: Cornelis Pieter Jan Visser, Warmond (NL)

(72) Inventors: Cornelis Pieter Jan Visser, Warmond (NL); Teake Hans Bulstra, Voorburg (NL)

(73) Assignee: IMPLANT SERVICE B.V., Vlaardingen (NL)

( * ) Notice: Subject to any disclaimer, the term of this patent is extended or adjusted under 35 U.S.C. 154(b) by 0 days.

(21) Appl. No.: 14/649,945

(22) PCT Filed: Oct. 9, 2013

(86) PCT No.: PCT/NL2013/050716
§ 371 (c)(1),
(2) Date: Jun. 5, 2015

(87) PCT Pub. No.: WO2014/058314
PCT Pub. Date: Apr. 17, 2014

(65) Prior Publication Data
US 2016/0166393 A1   Jun. 16, 2016

(30) Foreign Application Priority Data

Oct. 9, 2012   (NL) ...................................... 2009592

(51) Int. Cl.
*A61F 2/38*    (2006.01)
*A61B 17/68*   (2006.01)
(Continued)

(52) U.S. Cl.
CPC ............ *A61F 2/3804* (2013.01); *A61B 17/68* (2013.01); *A61B 17/72* (2013.01); *A61B 17/74* (2013.01);
(Continued)

(58) Field of Classification Search
CPC .. A61F 2/3804; A61F 2/40; A61F 2002/4007; A61F 2/4014; A61F 2002/4025;
(Continued)

(56) References Cited

U.S. PATENT DOCUMENTS 5,112,333 A    5/1992  Fixel
5,314,479 A *  5/1994  Rockwood, Jr. .......... A61F 2/40
                                                   623/19.14
(Continued)

FOREIGN PATENT DOCUMENTS

DE    10 2009 050 044 A1    4/2011
EP         1 398 000 A1     3/2004
(Continued)

OTHER PUBLICATIONS

International Search Report for PCT/NL2013/050716 Dated Nov. 8, 2011.
(Continued)

*Primary Examiner* — Alvin Stewart
(74) *Attorney, Agent, or Firm* — Nixon Peabody LLP; Jeffrey L Costellia (57) ABSTRACT

The invention provides an implantable medical device for treatment of a proximal humerus fracture, comprising a base element to be anchored in the medullar cavity of the humeral shaft, a support element to be fixed with respect to the base element, wherein the support element is configured to support one or more bone fragments, wherein the medical device comprises positioning members configured to position the support element with respect to the base element in
(Continued)

a range of rotational positions and axial positions, and wherein the medical device comprises a fixation device to fixate the support element, within the range of rotational positions and axial positions, in a desired rotational and axial position with respect to the base element. In an embodiment, the medical device is a non-occluding medical device, wherein after implantation the medullar cavity is not occluded by the medical device due to the open and non canal filling structure of the device preserving blood flow to the reattached bone fragments.

19 Claims, 3 Drawing Sheets (51) Int. Cl.
*A61B 17/72* (2006.01)
*A61B 17/74* (2006.01)

(52) U.S. Cl.
CPC ........... *A61F 2002/3822* (2013.01); *A61F 2220/0008* (2013.01)

(58) Field of Classification Search
CPC ............ A61F 2002/4029; A61F 2/4059; A61F 2002/407; A61F 2002/4077; A61F 2/38
USPC .......................................... 623/19.11–19.14
See application file for complete search history.

(56) References Cited

U.S. PATENT DOCUMENTS

| | | | | |
|---|---|---|---|---|
| 5,356,411 A * | 10/1994 | Spievack | ........... | A61B 17/7275 606/63 |
| 5,507,817 A | 4/1996 | Craig et al. | | |
| 5,658,350 A * | 8/1997 | Carbone | ............. | A61F 2/30723 606/95 |
| 5,658,351 A * | 8/1997 | Dudasik | ............. | A61F 2/30724 606/95 |
| 5,766,261 A * | 6/1998 | Neal | ................... | A61B 17/1659 606/85 |
| 5,766,262 A * | 6/1998 | Mikhail | ............. | A61B 17/8808 623/23.25 |
| 6,126,691 A * | 10/2000 | Kasra | .................... | A61F 2/3662 606/63 |
| 6,251,141 B1 * | 6/2001 | Pierson, III | ......... | A61F 2/30723 606/95 |
| 6,267,785 B1 * | 7/2001 | Masini | ............... | A61B 17/8802 606/92 |
| 6,334,874 B1 * | 1/2002 | Tornier | ................. | A61F 2/4059 623/19.11 |
| 6,336,929 B1 * | 1/2002 | Justin | ................. | A61B 17/7216 606/63 |
| 6,613,052 B1 * | 9/2003 | Kinnett | ................... | A61B 17/15 606/60 |
| 6,796,984 B2 * | 9/2004 | Soubeiran | .......... | A61B 17/7216 606/246 |
| 7,229,478 B2 * | 6/2007 | Masini | ............... | A61B 17/8802 623/19.11 |
| 7,481,841 B2 * | 1/2009 | Hazebrouck | .............. | A61F 2/36 623/18.12 |
| 8,623,092 B2 * | 1/2014 | Bickley | ..................... | A61F 2/40 623/18.11 |
| 2001/0011193 A1 | 8/2001 | Nogarin | | |
| 2005/0125067 A1 * | 6/2005 | Sweeney | ................... | A61F 2/36 623/19.14 |
| 2005/0187550 A1 | 8/2005 | Grusin | | |
| 2006/0004459 A1 * | 1/2006 | Hazebrouck | .............. | A61F 2/36 623/18.12 |
| 2006/0084999 A1 | 4/2006 | Aschmann | | |
| 2006/0142866 A1 * | 6/2006 | Baratz | ................... | A61F 2/3804 623/20.11 |
| 2010/0228357 A1 * | 9/2010 | Stauch | ................. | A61F 2/3607 623/23.47 |
| 2013/0197656 A1 * | 8/2013 | Conrad | ................. | A61F 2/4684 623/22.11 |

FOREIGN PATENT DOCUMENTS

| | | |
|---|---|---|
| EP | 1 676 538 A1 | 7/2006 |
| EP | 1 839 607 A2 | 10/2007 |
| EP | 2 431 008 A1 | 3/2012 |
| FR | 2 726 994 | 5/1996 |
| WO | WO 97/37606 A1 | 10/1997 |

OTHER PUBLICATIONS

European Office Action dated Feb. 24, 2016 issued in a European Pat. App. No. 13 777 162.2.
Chinese Office Action dated Mar. 2, 2016 issued in a Chinese Pat. App. No. 201380064215.3.
Written Opinion for PCT/NL2013/050716 dated Nov. 8, 2013.

* cited by examiner

MEDICAL DEVICE FOR RECONSTRUCTION OF A HUMERUS FOR THE OPERATIVE TREATMENT OF A PROXIMAL HUMERUS FRACTURE

The present invention relates to a medical device for reconstruction of a humerus for the operative treatment of a proximal humerus fracture.

BACKGROUND OF THE INVENTION

Proximal fractures of the humerus are fractures often related to osteoporosis, which occurs frequently in elder people. A proximal fracture of the humerus results in two or more fractured bone fragments. These bone fragments may comprise the humeral head, the humeral shaft, and the greater or lesser tuberosity.

If the bone fragments of the broken humerus are still properly positioned after the fracture, the patient may be successfully treated without surgery. If the bone fragments are dislocated, the position of the bone fragments is often unfavourable so that non-operative treatment would lead to incorrectly or no growing together of the bone fragments.

In those cases the results are generally quite poor and lead to permanent stiffness, pain and limitation of shoulder movements and possibly invalidity of a person. Subsequent interventions to this problem generally do not provide further improvement. Re-operations for bone fractures of a humerus fracture which are not or incorrectly grown together, rarely lead to good results.

A proper reconstruction of the humerus, wherein the bone fragments are relocated to and fixed substantially in their original positions is an important aspect in the treatment of humerus fractures. A fracture in a good position gives a significantly better result than a fracture healing in a bad position.

Various techniques for surgical treatment are used, such as pin- or plate osteosynthesis, K-wire osteosynthesis, screw fixation, suture techniques (cerclage) and treatment by placement of a shoulder prosthesis. Although these techniques are used successfully in some cases, relatively high rates of complications and problems are described in literature. In the existing fixation techniques is frequently seen that the surgery is not sufficient.

Reasons for a low success rate of operation results are for example the weak bone of the humerus in older people, the weak structure of the humerus in general (not weight-bearing joint), the disruption of the vascularization (blood flow) of the humeral head due to the fracture and the difficult surgical technique.

In view of the problems encountered in the known techniques for reconstruction of the humerus in the treatment of a humeral fracture, there is a need to provide new techniques for reconstruction of the humerus, which make proper and reliable reconstruction of the humerus possible.

SUMMARY OF THE INVENTION

An aim of the present invention is to provide an implantable medical device for reconstruction of a humerus for treatment of a proximal humerus fracture, which provides flexibility during the reconstruction of the humerus of a patient. This flexibility makes a more efficient treatment of a proximal fracture of the humerus possible, in particular when the humerus is broken in three or more bone fragments.

The invention provides an implantable medical device for reconstruction of a humerus as treatment of a proximal humerus fracture, comprising:
- a base element to be anchored in the medullar cavity of the humeral shaft,
- a support element to be fixed with respect to the base element, wherein the support element is configured to support one or more bone fragments,
- wherein the medical device comprises positioning members configured to position the support element with respect to the base element in a range of rotational positions and axial positions, and in that
- the medical device comprises a fixation device to fixate the support element, within the range of rotational positions and axial positions, in a desired rotational and axial position with respect to the base element.

The medical device of the invention makes an efficient and reliable reconstruction of the fractured humerus possible, in particular in complex fractures where the proximal end of the humerus is fractured in three or more bone parts.

The base element can be anchored in the medullar cavity of the humeral shaft. The medullar cavity of the humeral shaft may usually provide a good support for anchoring of the medical device.

When the base element is anchored in the medullar cavity at a fixed position, the positioning members, for example a positioning device, make it possible that the support element which is used for supporting one or more further bone fragments, in particular the greater and lesser tuberosity and/or the humeral head, can still be moved in a range of positions in both rotational and axial directions. In any of these rotational and axial positions the support element can be fixed to the base element by the fixation device, resulting in a fixed position of the support element with respect to the humeral shaft.

With this construction, the positioning of the support element with respect to the humerus is made, within the range of rotational and axial positions, independent of the anchoring of the medical device in the medullar cavity of the humerus. The position of the support element can be selected on the basis of the desired positions of the further bone parts, such as the greater and lesser tuberosity and/or the humeral head after reconstruction of the humerus.

Once the support element is fixed in the desired position with respect to the base element and the humeral shaft in which the base element is anchored, the one or more bone fragments may be supported by the support element. The one or more bone parts may also be secured to the support element. Any suitable technique may be used to fix the bone parts to the support element, for example suture techniques, in particular cerclage.

After reconstruction, the medical device itself provides support to the bone fragments, and the bone fragments may be attached to the support element.

Because the interior of the proximal humerus is filled with the medical device it is prevented that the possibly thin and porous bone fragments will damage or break during or after fixation of the bone fragments on the medical device.

In an embodiment, the base element is configured to be easily removable, if necessary, for example when it is desired to replace the medical device in a next operation with an alternative prosthesis.

In an embodiment, the medical device is configured to provide after implantation at least one fluid communication channel that provides fluid communication, in particular a blood flow, between the medullar cavity of the humeral shaft and the one or more bone fragments, such as for example the humeral head. Such medical device may provide at least one fluid communication channel that provides fluid communication between a distal end and a proximal end of the device.

The present invention relates to a medical device that is used for reconstruction of the humerus after a proximal humerus is fractured. In such reconstruction, the bone fragments resulting from the fracture can be repositioned and fixed to the medical device for healing of the bone fragments of the proximal humerus in the desired position.

The reconstruction typically at least comprises the repositioning and fixation of the humeral head and/or other bone parts such as the greater or lesser tuberosity in a desired position. The reconstruction may also involve repositioning and fixation of some bone parts, and replacement of the humeral head by an artificial humeral head.

For a proper healing of the proximal humerus after reconstruction, it is desirable that reattached bone fragments, for example the humeral head are provided with sufficient blood. This blood is typically provided from the endosteum, an inner layer of the medullar cavity, and (longitudinal) blood vessels in the medullar cavity. Therefore, the device is preferably configured to provide a fluid communication channel, i.e. a blood supply channel that provides a blood supply from the medullar cavity to the one or bone fragments after reconstruction. The channel may be filled with original bone material such as marrow, and the channel may be delimited by bone material, in particular by the inner surface of the medullar cavity, and/or the medical device. Generally, the fluid communication channel may be provided by preservation of a part of the original bone structure of the medullar cavity of the humeral shaft.

The medical device may be a non-occluding medical device, i.e. after implantation, the medical device does not occlude the medullar cavity (intramedullary canal) of the humerus. As the medullar cavity is not occluded by the medical device, in particular due to an open and non-medullary canal filling structure of the medical device, blood supply from the medullar cavity in the humeral shaft to the reattached bone fragments is preserved. The medical device is preferably configured to allow, after implantation/reconstruction, a blood flow from a part of the medullar cavity arranged distally of the medical device to bone parts arranged proximally of or at a proximal end of the medical device.

Prior art prostheses to be placed in the medullar cavity having replacement bone parts such as a humeral head, and which do not require healing of one or more bone parts typically do not need blood provision to the humeral head and typically have anchoring devices that block the medullar cavity, such as a pen having a diameter corresponding to the medullar cavity and/or cementing of the medullar cavity. Anchoring such a pen into the medullar cavity damages the blood transport to the proximal end of the humerus. When using a cement to anchor a prosthesis, the blood canals are further damaged by heat used to harden the cement. As a result, blood cannot flow from the medullar cavity to the proximal end of the humerus.

In an embodiment, the positioning members comprise a cylindrical opening in one of the base element and the support element, and a cylindrical extension at the other of the base element and the support element.

In such embodiment, the inner diameter of the cylindrical opening may substantially correspond or be smaller than the outer diameter of the cylindrical extension so that the cylindrical extension can be at least partially arranged in the cylindrical opening.

The combination of a cylindrical opening and a cylindrical extension, which are telescopically arranged with respect to each other, provide a relative simple and reliable mechanism creating a range of rotational and axial positions providing a large range of freedom of movement to position the support element with respect to the base element.

The cylindrical shapes of extension and opening make relative rotation over the whole circumference possible, while the extent of overlapping of the extension and the opening defines the axial range of movement of the support element with respect to the base element. The relative rotation of the cylindrical opening and the cylindrical extension may be limited by one or more rotation limiting elements to a part of the circumference, i.e. smaller than 360 degrees, for instance by rotation stops. The axial range may also be limited by stops or other elements.

In an embodiment, the positioning members comprise at the distal end of the support element a tube-shaped part defining a cylindrical opening, and at the proximal end of the base element a cylindrical extension, wherein an outer diameter of the cylindrical extension substantially corresponds to an inner diameter of the cylindrical opening.

The cylindrical opening of the support element preferably is a through opening, such that the proximal part of the cylindrical extension can be reached from the proximal side of the support element through the cylindrical opening. The outer diameter of the cylindrical extension and the inner diameter of the cylindrical opening are preferably selected such that the base element will hold the support element when no other force is exerted on the support element, while at the same time the support element can be moved with respect to the base element with a little force.

The friction between the cylindrical extension and the cylindrical opening is preferably kept at a low level so that relative positioning of the support element with respect to the base element can be done with high accuracy. The friction may also be reduced by providing materials having a low friction on or in the respective surfaces of the cylindrical extension and the cylindrical opening.

In an embodiment, the fixation device comprise a fixation element to be placed in the proximal end of the base element, which fixation element is configured to increase the outer diameter of the cylindrical extension when placed in the proximal end of the base element.

When the diameter of the cylindrical extension can be increased by placing a fixation element in the cylindrical extension, the cylindrical extension can be clamped in the cylindrical opening. This fixation of the support element with respect to the base element is performed when the support element is positioned in a desired position with respect to the base element and humeral shaft during reconstruction of the humerus.

Such clamping device may for example be obtained by providing a cylindrical extension having two diametrically opposed extension parts extending in the axial direction which are movably radially outwards by the fixation element, wherein preferably the fixation element is a screw element having an outer screw thread, and wherein the two extension parts having an inner screw thread to cooperate with the outer screw thread.

It is remarked that the fixation element may also be used to adjust a friction during positioning between cylindrical extension and cylindrical opening in agreement with the wishes of the surgeon.

In an embodiment, a distal end of the base element comprises one or more anchor elements extending in radial direction over a limited part of the circumference of the base element to anchor the base element in the medullar cavity of the humerus. By providing one or more anchor elements extending in radial direction over a limited part of the circumference a proper anchoring of the base element in the medullar cavity may be obtained. At the same a substantial part of the circumference of the base element is not blocked by the one or more anchor element. These parts of the medullar cavity that are not blocked form longitudinal channels in the medullar cavity. These longitudinal channels are advantageous as they enable blood to flow in longitudinal direction past the medical device. Blood flow is of high importance for the healing of the bone fragments of the humerus.

The term over a limited part of the circumference means in this application that the one or more anchor elements do not extend radially over the complete circumference therewith blocking the medullar cavity. Furthermore, the limited part of the circumference may be divided over a plurality of sub-parts divided over the circumference of the base element.

In addition, or as an alternative, the base element may comprise one or more through going channels which run between proximally of the one or more anchor element and distally of the one or more anchor elements to allow a blood flow past the one or more anchor elements. The one or more through going channels may for example be provided in the one or more anchor elements and/or in a main body of the base element.

In an embodiment, the one or more anchor elements provide sufficient anchoring force for anchoring of the medical device. This means that no additional anchoring devices or materials are required, such as cementing of the medical device, to properly anchor the medical device in the medullar cavity. This is desirable as the additional anchoring devices or materials may hinder blood flow from the medullar cavity to the bone fragments.

In an embodiment, the one or more anchor elements comprise at least three fins divided over the circumference of the base element and extending in a plane perpendicular to a tangential direction. The fins may be at or near the distal end of the base element. The radial dimensions of the fins are selected such that the fins provide a proper anchoring of the base element in the medullar cavity.

The fins are preferably stiff but thin so that the fins block the medullar cavity in axial direction as little as possible.

Before anchoring of the base element in the medullar cavity, the radial extent of the fins may be adapted to the required radial extent of the fins for proper anchoring of the base element in the medullar cavity, without requiring excessive force to bring the base element in the medullar cavity or having the risk of damaging the anchor fins or bone. The fins may for instance be clipped or cut to the desired radial dimensions.

In an embodiment, the base element at least between the one or more anchor elements tapers in the distal direction. By tapering of the base element in the distal direction between the anchor elements, the cross section of the medullar cavity which is not occupied by the base element may be increased, therewith creating more space for a blood flow between a distal end and a proximal end of the one or more anchor elements.

In an embodiment, the support element comprises a cage for fixation of one or more bone fragments. The support element may be used for support for and fixation of the one or more bone parts in the respective desired locations. A cage provides a relative large volume with several possibilities to attach the one or more bone parts to the cage. The cage may for example be formed as an open construction having struts for attachment of loops or use of K-wires or other attachments devices or suture material for the fixation of one or more bone fragments.

Any other device or means for support and/or fixation of the one or more bone parts may also be provided.

In an embodiment, the cage is formed to substantially fill the interior of a proximal end of a humerus to be treated. The cage preferably fills substantially the interior of the proximal end of the humerus, so that when the one or more bone parts are placed against the cage for support and fixation, the one or more bone parts are properly positioned for a successful reconstruction of the humerus.

In an embodiment, the medical device, preferably the cage, defines a humeral head support plane to support the humeral head. To properly position, during reconstruction of the humerus, the humeral head with respect to the support element, a support plane is formed for supporting the humeral head. This support plane is angled with respect to the longitudinal axis of the medical device with an angle substantially corresponding to an angle in which the humeral head should be located with respect to the longitudinal axis of the humeral shaft. This angle substantially corresponds to the angle of the anatomical neck of the humerus.

It is remarked that the humeral head support plane may also be defined by any other suitable part of the medical device of the invention.

The humeral head positioning element may for example be arranged on the humeral head support plane or may be an integral part of the support element.

In an embodiment, the medical device comprises one or more protrusions which project from the support plane, the protrusions being configured to at least partially penetrate the humeral head. One or more, for example three, protrusions projecting from the humeral head support plane may be provided to at least partially penetrate into the bone structure of the humeral head to provide or improve a connection between the humeral head and the medical device. The one or more protrusions may have any suitable shape.

In such embodiment, the one or more protrusions may for example be formed on one or more struts of a cage element.

The protrusions may be pointed or sharpened to facilitate penetration of the bone structure of the humeral head.

Further protrusions may be provided to penetrate other bone fragments of the fractured humerus.

In an embodiment, the medical device comprises a humeral head positioning element configured to be at least partially arranged in the humeral head for positioning of the humeral head with respect to the support element. For further support of the humeral head, a humeral head positioning element may be provided which may provide internal support to the humeral head.

In an embodiment, the medical device could be made of biodegradable material.

After reconstruction of a humerus using the medical device of the invention, the medical device is enclosed by the humerus and will remain therein. After the bone fragments are healed to a single bone structure, the medical device may no longer be required in the humerus. By forming the medical device from a biodegradable material, the medical device can be degraded or decomposed after a certain period of time so that no body foreign material remains. It may be desirable to use a hybrid type of device in which parts are made of biodegradable material and parts are made of non-biodegradable material. In an embodiment, it may for example be possible that the base element is made of a non-biodegradable material, for example a metal, while the other parts are made of biodegradable material. Such embodiment provides the possibility to use the base element to support, when desired, a new support element. In such embodiment, a screw element to be screwed in the base element may also be of non-biodegradable material such that the screw element, when desired, can reliably be removed from the base element. Any other suitable combination of biodegradable and non-biodegradable parts may also be applied.

In an alternative embodiment, it may be desirable that the medical device remains in the humerus to provide permanent support to the bone structure of the proximal humerus end from the interior.

The medical device may also comprise a material which stimulates bone growth, so that the presence of the material of the medical device improves healing of the bone.

The present invention also relates to a method to treat a proximal humerus fracture, comprising the steps of: providing an implantable medical, comprising:
  a base element to be anchored in the medullar cavity of the humeral shaft,
  a support element to be fixed with respect to the base element, wherein the support element comprises a cage for fixation of one or more bone fragments,
wherein the medical device comprises positioning members configured to position the support element with respect to the base element in a range of rotational positions and axial positions, and wherein the medical device comprises a fixation device to fixate the support element, within the range of rotational positions and axial positions, in a desired rotational and axial position with respect to the base element,
anchoring a distal end of the base element in the medullar cavity of the humerus,
positioning by the positioning members the support element, within the range of rotational and axial positions, in a desired position with respect to the base element,
fixing by the fixation device the support element with respect to the base element, and
reconstructing the humerus by fixing one or more fractured bone fragments of the fractured humerus to the support element.

According to another aspect, the invention provides an implantable medical device for reconstruction of a humerus as treatment of a proximal humerus fracture, comprising:
  a base element to be anchored in the medullar cavity of the humeral shaft,
  a support element to be fixed with respect to the base element, wherein the support element is configured to support one or more bone fragments,
wherein the medical device is configured to provide after implantation at least one fluid communication channel that provides fluid communication between the medullar cavity and the one or more bone fragments, in particular the humeral head in order to supply blood to the one or more bone fragments after reconstruction of the humerus.

The medical device may be provided with one or more of the features of the dependent claims 1-18.

BRIEF DESCRIPTION OF THE DRAWINGS

An embodiment of an implantable medical device according to the invention will now be described in further detail, by way of example only, with reference to the accompanying drawings, in which.

DESCRIPTION OF PREFERRED EMBODIMENTS

Figure 1:
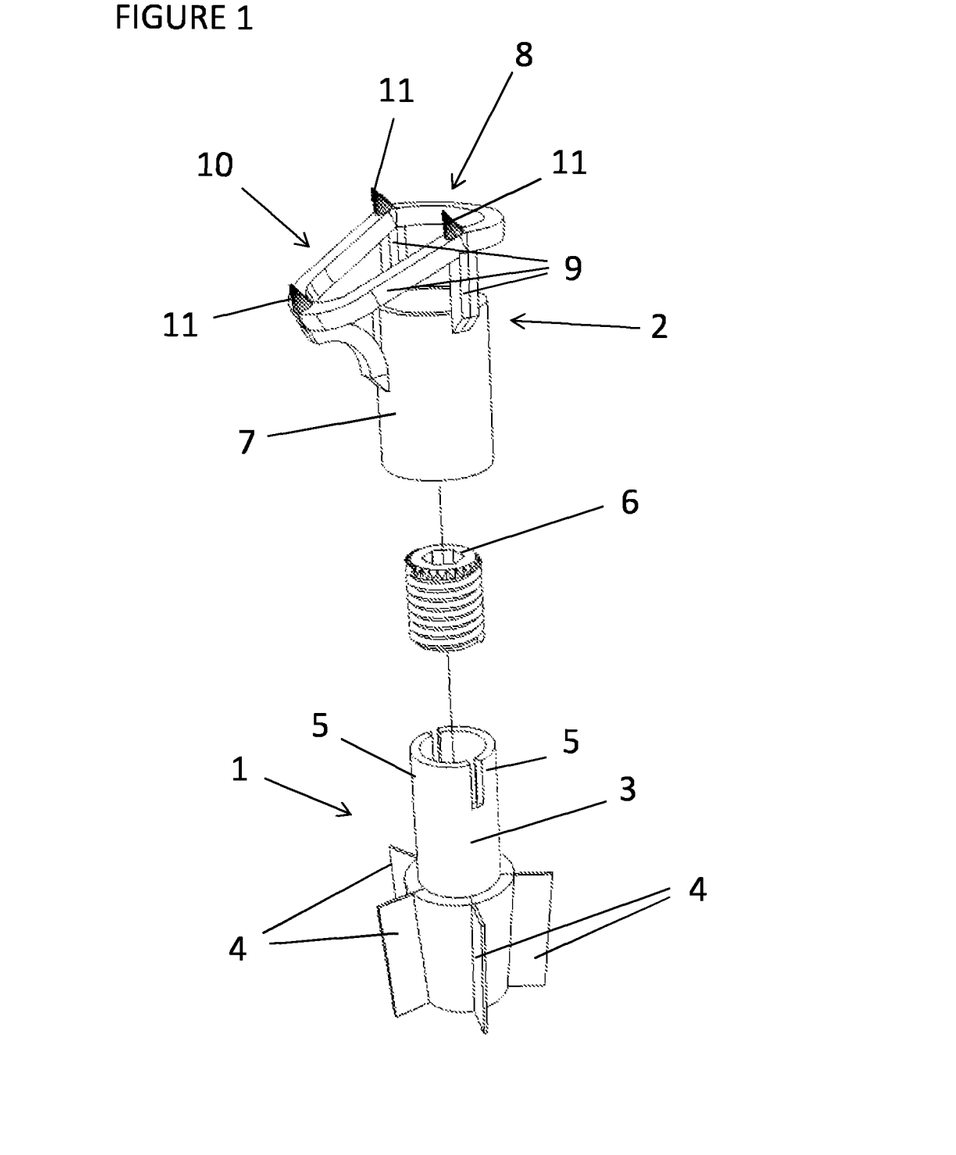
FIG. 1 shows, in perspective view, an embodiment of a disassembled medical device according to the invention.

FIG. 1 shows an embodiment of an implantable medical device according to the invention in disassembled and perspective view. The medical device is configured for treatment of a proximal humerus fracture and comprises a base element 1 to be anchored in the medullar cavity of a humeral shaft of a humerus to be treated and a support element 2 configured to support one or more bone fragments of the humerus.

The base element 1 comprises a base element body forming a cylindrical extension 3 at its proximal end. The distal end of the base element 1 comprises five anchor fins 4 divided over the circumference of the base element. The anchor fins 4 extend in radial direction and are configured to anchor the base element 1 in the bone of the humeral shaft surrounding the medullar cavity of the humeral shaft.

The anchor fins 4 are thin walled but stiff elements which provide for proper anchoring of the base element 1 in the medullar cavity. The anchor fins are arranged over a limited part of the circumference of the base element 1, and the anchor fins 4 will only partly enter into the bone of the humeral shaft so that space will remain between the base element body and the inner wall of the humeral shaft.

This space is advantageous for blood flow past the base element in longitudinal direction which is important for proper healing of the humerus. In addition, or as an alternative, blood may also flow between a distal end and a proximal end of the base element through one or more internal channels in the base element.

The proximal end of the cylindrical extension 3 comprises two diametrically opposed extension parts 5 extending in the axial direction which are movably radially outwards by a screw element 6, having an outer screw thread, which cooperates with an inner screw thread arranged on the inner sides of the extension parts 5.

The support element 2 comprises at its distal end a cylindrical tube 7 having an inner diameter which substantially corresponds with the outer diameter of the cylindrical extension 3. The outer diameter of the cylindrical extension 3 is slightly smaller than the inner diameter of the cylindrical tube 7, when the screw element 6 is not screwed between the extension parts 5. However, when the screw element 6 is screwed between the extension parts 5, the extension parts 5 will be moved away from each other, therewith increasing the diameter of the cylindrical extension 3 to a diameter larger than the inner diameter of the cylindrical tube 7. In alternative embodiments, more than two extension parts 5 may be provided The cylindrical tube 7 can be placed about the cylindrical extension 3 in a telescopic manner. The cylindrical tube 7 can be moved with respect to the cylindrical extension over a range of rotational and axial positions, while the screw element 6 makes it possible to fixate the support element 2 with respect to the base element 1 in any of these positions within this range.

This gives the surgeon performing a reconstruction of the proximal humerus the possibility to adjust the position of the support element 2 within a range of rotational and axial positions after the base element 1 has been anchored in the medullar cavity by the anchor fins 4. Once the surgeon has positioned the support element 2 in the desired position, the support element 2 may be fixed in this position by screwing the screw element 6 into the base element 1 between the extension parts 5. A screw tool 40 (FIG. 4) is provided for rotating the screw element 6. The support element 2 comprises a longitudinal channel so that the screw element 6 can be reached from the proximal end of the medical device.

The proximal end of the support element 2 comprises a cage 8 formed by struts 9 as an open construction. This open construction may improve blood flow from the medullar cavity to the different bone parts.

The cage 8 is formed to substantially fill the interior cavity of the proximal end of the humerus, so that the one or more bone parts can be placed against the support surfaces of the cage 8 for support and fixation, therewith also placing the one ore more bone parts in the desired position for a proper reconstruction of the humerus.

The struts 9 can advantageously be used for attachment of loops of K-wires or other attachments devices or suture material for the fixation of one or more bone fragments to the cage 8.

The cage 8 forms support surfaces for the bone parts such as the greater and lesser tuberosities and the humeral head.

The cage 8 for example defines a humeral head support plane 10 to support the humeral head. This support plane 10 is angled with respect to the longitudinal axis of the medical device with an angle substantially corresponding to an angle in which the humeral head should be located with respect to the longitudinal axis of the humeral shaft.

On the humeral head support plane 10 three pointed protrusions 11 are provided. The protrusions 11 are formed on the strut elements 9 of the cage 8. The protrusions 11 project from the humeral head support plane 10 and are provided to at least partially penetrate the bone structure of the humeral head to improve the connection between the cage 8 and the humeral head. Other protrusions may also be provided at any suitable location, for instance to at least partially penetrate other bone fragments of a fractured humerus.

As an alternative, or in addition, a humeral head positioning element may be provided. The humeral head positioning element may be placed in the humeral head for further support in the positioning of the humeral head with respect to the cage 8. Usually, the humeral head comprises a cavity having internal dimensions. It has been found that it may be advantageous to provide a humeral head positioning element being substantially smaller than this internal dimensions. This provides some freedom to reposition the humeral head at the end of the reconstruction, since the position of the humeral head is not completely dictated by the cage 8 and the humeral head positioning element provided thereon.

The elements of the medical device may be made from any suitable material, such as for example biocompatible plastics material. The medical device may be made of biodegradable material, so that after the reconstructed humerus has healed, the material of the medical device may degrade or decompose. However, the medical device may also be configured to remain within the humerus for permanent support of the proximal end of the humerus from the interior. Support from the interior has the advantage that the presence of the medical device does not hamper functioning of other parts of the body, such as ligaments or muscles.

It is desirable that the base element 1 is removable from the medullar cavity when required, for example in the case of a prosthesis replacement in the future. The anchor fins 4 provide such removable medical device.

The medical device of the invention makes an efficient and reliable reconstruction of a fractured humerus possible, in particular in complex fractures where the proximal end of the humerus is fractured in three or more bone parts. These bone parts typically comprise the humeral shaft, the humeral head and one or both of the greater and lesser tuberosities.

The different steps for placing the medical device in a proper position in the humerus will now be discussed.

As a first step, the base element 1 is anchored in the medullar cavity of the humeral shaft. This anchoring is performed by forcing from the proximal side the base element 1 into the medullar cavity, while the anchor fins 4 at least partly penetrate into the bone of the humeral shaft.

Figure 2:
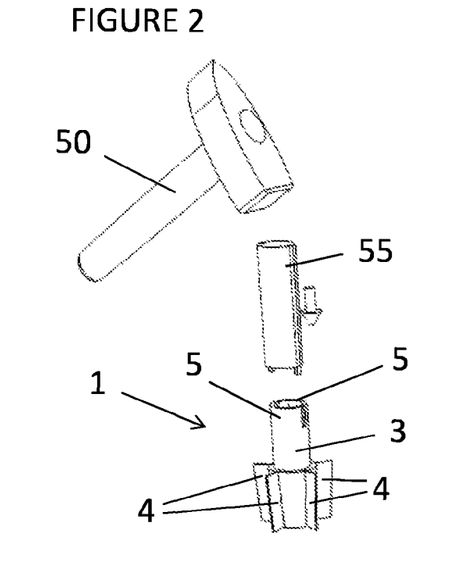
FIGS. 2-5 show the build-up of the medical device of FIG. 1 during treatment of a proximal humerus fracture.

FIG. 2 shows a hammer 50 and a rod element 55 with which the base element 1 can be hammered into the medullar cavity in the direction indicated by an arrow. The rod element 55 comprises longitudinal ribs the ends of which can be positioned into slots of the base element 1 to properly engage the rod element 55 and the base element 1 during anchoring of the base element 1.

Before actual anchoring of the base element 1 in the medullar cavity, the radial extent of the anchor fins 4 may be adapted, for example by clipping or cutting, to adapt the anchor fins 4 to the required diameter for proper anchoring of the base element 1 in the medullar cavity, without requiring excessive force.

Figure 3:
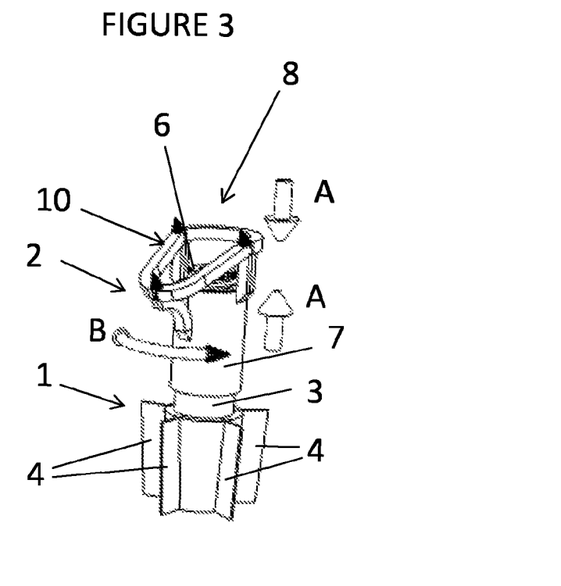

When the base element 1 is properly anchored in the humeral shaft, the cylindrical tube 7 of the support element 2 may be placed over the cylindrical extension 3 of the base element 3 in a telescopic arrangement as shown in FIG. 3.

The telescopic arrangement of cylindrical tube 7 and cylindrical extension 3 provide a range of rotational and axial positions in which the support element 2 can be positioned with respect to the base element 1. The freedom of movement of the support element 2 with respect to the base element 1 is indicated in FIG. 3 by arrows A in longitudinal direction and B in rotation direction. The desired position of the support element 2 is the position in which the cage 8 provides the best start position for reconstruction of the humerus.

Figure 4:
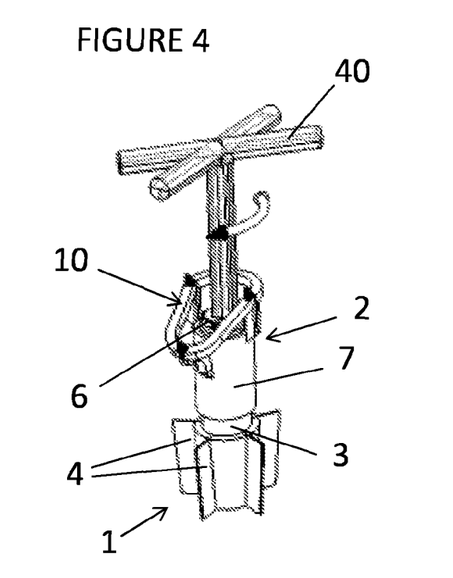

When the support element 2 is positioned in this desired position, the support element 2 can be fixated with respect to the base element 1 by screwing the screw element 6 with screw tool 40 into the base element 1 between the extension parts 5, as shown in FIG. 4. In practice, the screw element 6 may already be partly brought into the base element 1, so that the screw element 6 can directly be screwed further into the base element 1 without the need of aligning the outer screw thread of the screw element 6 with the inner screw thread of the extension parts 5. This pre-placement, may be advantageous as the aligning may have the consequence that the support element 2 is moved out of the desired position by manipulation of the screw element in the support element 2.

It is remarked that the presence of the screw element 6 in the base element 1 can also be used to set a friction level between the cylindrical tube 7 and the cylindrical extension 3, which is regarded by the surgeon as pleasant during positioning of the support element 2 with respect to the base element 1.

After the support element 2 is fixated, the position of the cage 8 can be checked. When required, the support element 8 may be repositioned by unscrewing the screw element 6 so that the support element 2 and the base element 1 are again movable with respect to each other.

Figure 5:
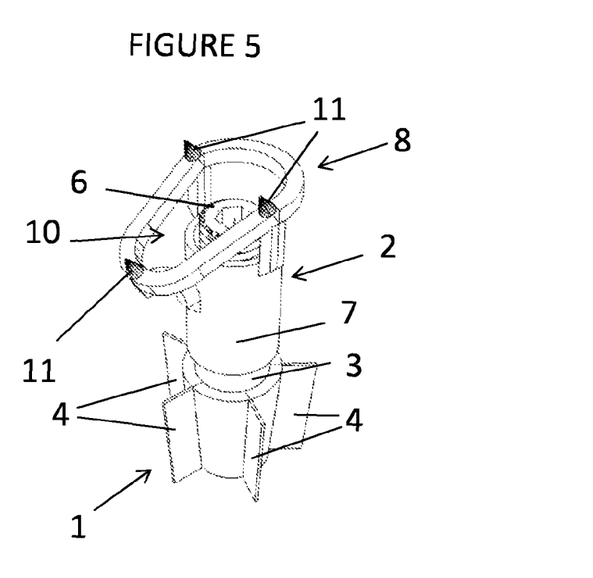

FIG. 5 shows the medical device after fixation of the base element 1 and the support element 2 with respect to each other and after removal of the screw tool 40.

When the surgeon has determined that the support element 2 and therewith the cage 8 is positioned in a proper start position for reconstruction of the humerus, the reconstruction can be started. When desired a humeral head positioning element can be arranged on and when desired attached to the humeral head support plane 10.

During reconstruction the one or more fractured bone fragments of the fractured humerus can be fixed to the cage 8. The struts 9 of the cage 8 provide a plurality of attachment locations for attachment materials such as K-wires or suture material. The medical device, in particular the cage 8, provides a proper support for repositioning and fixation of the bone parts. The humerus head may be supported by the humerus head support plane 10, where it is placed on the protrusions 11. The protrusions 11 may at least partially penetrate the bone structure of the humerus head to improve the connection between the humerus head and the medical device.

After the reconstruction of the humerus has been finished, the arm of the patient can be fixated so that the humerus may heal.

Figure 6:
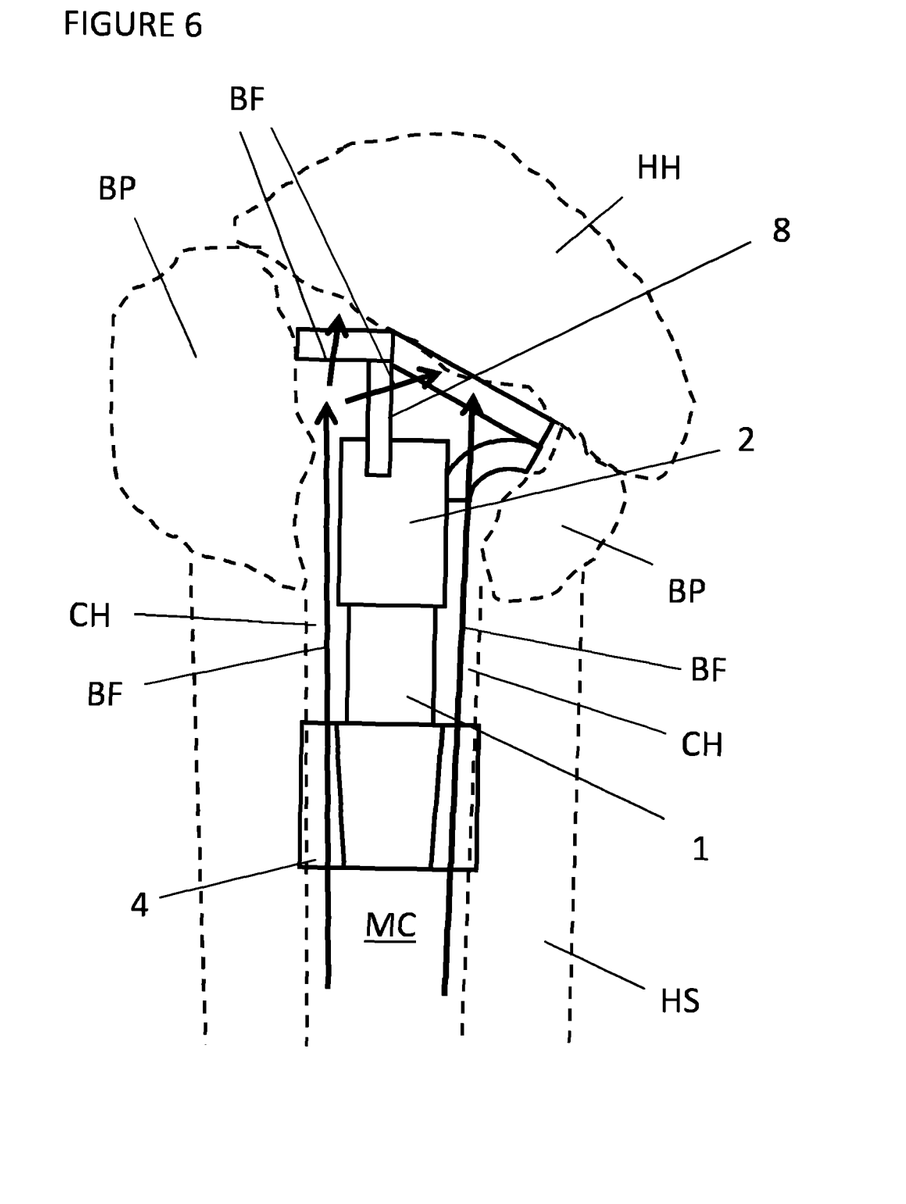
FIG. 6 shows the medical device schematically after implantation.

FIG. 6 shows schematically the medical device of FIG. 1 after implantation of the medical device in a humerus of a patient with a humerus fracture.

The humerus fracture has resulted in different bone parts including the humeral shaft HS, the humeral head HH and other bone parts BP.

The medical device is implanted in the way described above, wherein first the base element 1 is anchored by anchor fins 4 in the medullar cavity MC of the humeral shaft HS, such that the base element 1 is sufficiently anchored for reconstruction of the humeral fracture using the medical device without the need of other anchoring devices, means or materials.

After the base element 1 was anchored, the support element 2 was placed on the base element 1 and placed in a proper position for reconstruction of the humerus fracture, and subsequently fixated in this position. Thereafter, the humeral head HH and other bone parts BP were repositioned around the support element 2 to reconstruct the proximal end of the humerus. In these positions the humeral head HH and other bone parts BP were fixed to the support part 2 to substantially hold these parts in their positions.

As can be seen in FIG. 6, the medical device, and in particular the cage 8 of the support element 2 fills substantially the interior of the proximal end of the humerus, and provides a suitable support for the humeral head HH and other bone parts BP in a desired position for reconstruction. This facilitates the fixation of the humeral head HH and other bone parts BP to the support element 2 and improves the possibilities to maintain the humeral head HH and other bone parts BP in the desired positions for reconstruction.

Further, it can be seen in FIG. 6, that the medical device is configured to provide, after implantation, fluid communication channels CH that provide fluid communication between the medullar cavity MC and the humeral head HH and bone parts BP. These channels CH provide the possibility for blood supply from the medullar cavity MC of the humeral shaft distally of the medical device to the humeral head HH and bone parts BP arranged at the proximal end of the medical device. The provision of blood to these parts is important for the healing of the humeral head HH and other bone parts BP, and the humerus fracture in general.

An example of the blood flow through the channels CH is indicated by arrows BF. It can be seen that the anchor fins 4 that only use a limited part of the circumference of the base element 1 to properly anchor the device in the medullar cavity MC, make a blood flow past the distal end of the device possible. The placement of these anchor fins 4 did not completely damage the original blood supply to the proximal end of the humerus, as a substantial part of the original bone structure is preserved. The open construction of the cage 8 provides space for blood flow to the humeral head HH and bone parts BP at the proximal end of the device. As a result of this construction of the medical device, blood flow through the channels CH, in particular through the original blood supply vessels, from a distal end of the device to a proximal end of the device is facilitated, which improves healing of the humerus fracture.

It is remarked that other constructions to provide a fluid communication channel that provides fluid communication between the medullar cavity and the one or more bone fragments, in particular the humeral head may also be applied. For example, the device may comprise internal channels to guide blood from the distal end to the proximal end of the device, although it is preferred to partly preserve the original bone structure for blood supply to the proximal humerus end.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. Implantable medical device for reconstruction of a humerus for treatment of a proximal humerus fracture, comprising:
   a base element to be anchored in the medullar cavity of the humeral shaft,
   a support element to be fixed with respect to the base element, wherein the support element is configured to support one or more bone fragments,
   wherein the medical device comprises positioning members configured to position the support element with respect to the base element in a range of rotational positions and axial positions,
   wherein the medical device comprises a fixation device to fixate the support element, within the range of rotational positions and axial positions, in a desired rotational and axial position with respect to the base element, and
   wherein a distal end of the base element comprises one or more anchor elements extending in radial direction to anchor the base element in the medullar cavity of the humerus.

2. Medical device according to claim 1, wherein the medical device is configured to provide after implantation at least one fluid communication channel that provides fluid communication between the medullar cavity of the humeral shaft and the one or more bone fragments.

3. Medical device according to claim 1, wherein the medical device is a non-occluding medical device, wherein after implantation the medullar cavity is not occluded by the medical device.

4. Medical device according to claim 1, wherein the positioning members comprise a cylindrical opening in one of the base element and the support element, and a cylindrical extension at the other of the base element and the support element.

5. Medical device according to claim 1, wherein the positioning members comprise at the distal end of the support element a tube-shaped part defining a cylindrical opening, and at the proximal end of the base element a cylindrical extension, wherein an outer diameter of the cylindrical extension substantially corresponds to an inner diameter of the cylindrical opening.

6. Medical device according to claim 5, wherein the fixation device comprise a fixation element to be placed in the proximal end of the base element, which fixation element is configured to increase the outer diameter of the cylindrical extension when placed in the proximal end of the base element.

7. Medical device according to claim 6, wherein the cylindrical extension comprises two diametrically opposed extension parts extending in the axial direction which are movably radially outwards by the fixation element.

8. Medical device according to claim 7, wherein the fixation element is a screw element having a outer screw thread, and wherein the two extension parts having an inner screw thread to cooperate with the outer screw thread.

9. Medical device according to claim 1, wherein the one or more anchor elements provide sufficient anchoring force for anchoring of the medical device.

10. Medical device according to claim 1, wherein the one or more anchor elements comprise at least three fins divided over the circumference of the base element and extending in a plane perpendicular to a tangential direction.

11. Medical device according to claim 1, wherein the base element at least between the one or more anchor elements tapers in the distal direction.

12. Medical device according to claim 1, wherein the support element comprises a cage for fixation of one or more bone fragments.

13. Medical device according to claim 12, wherein the cage is formed to substantially fill the interior of a proximal end of a humerus to be treated.

14. Medical device according to claim 12, wherein the cage is formed as an open construction having struts for attachment of loops or use of K-wires or other attachment devices for the one or more bone fragments.

15. Medical device according to claim 1, wherein the medical device defines a support plane to support a humeral head of the humerus.

16. Medical device according to claim 15, wherein the medical device comprises one or more protrusions which project from the support plane, the protrusions being configured to at least partially penetrate the humeral head.

17. Medical device according to claim 1, wherein the medical device is made of biodegradable material.

18. Implantable medical device for reconstruction of a humerus as treatment of a proximal humerus fracture, comprising:

a base element to be anchored in the medullar cavity of the humeral shaft,
a support element to be fixed with respect to the base element, wherein the support element is configured to support one or more bone fragments,
wherein the medical device comprises positioning members configured to position the support element with respect to the base element in a range of rotational positions and axial positions,
wherein the medical device comprises a fixation device to fixate the support element, within the range of rotational positions and axial positions, in a desired rotational and axial position with respect to the base element, and
wherein the medical device is configured to provide after implantation at least one fluid communication channel that provides fluid communication between the medullar cavity of the humeral shaft and the one or more bone fragments.

19. A method to treat a proximal humerus fracture, comprising the steps of:
providing an implantable medical, comprising:
a base element to be anchored in the medullar cavity of the humeral shaft,
a support element to be fixed with respect to the base element, wherein the support element comprises a cage for fixation of one or more bone fragments,
wherein the medical device comprises positioning members configured to position the support element with respect to the base element in a range of rotational positions and axial positions, and wherein the medical device comprises a fixation device to fixate the support element, within the range of rotational positions and axial positions, in a desired rotational and axial position with respect to the base element,
anchoring a distal end of the base element in the medullar cavity of the humerus,
positioning by the positioning members the support element, within the range of rotational and axial positions, in a desired position with respect to the base element,
fixing by the fixation device the support element with respect to the base element, and
reconstructing the humerus by fixing one or more fractured bone fragments of the fractured humerus to the support element, wherein the medical device after implantation provides at least one fluid communication channel that provides fluid communication between the medullar cavity of the humeral shaft and the one or more bone fragments.

* * * * *